United States Patent
Flodin

(10) Patent No.: US 7,464,711 B2
(45) Date of Patent: Dec. 16, 2008

(54) DEVICE FOR A RESPIRATOR

(76) Inventor: Björn Flodin, Tallåasvägen 8-10, Spånga SE-163 43 (SE)

( * ) Notice: Subject to any disclaimer, the term of this patent is extended or adjusted under 35 U.S.C. 154(b) by 90 days.

(21) Appl. No.: 10/471,563

(22) PCT Filed: Mar. 14, 2002

(86) PCT No.: PCT/SE02/00486

§ 371 (c)(1), (2), (4) Date: Jan. 28, 2004

(87) PCT Pub. No.: WO02/072184

PCT Pub. Date: Sep. 19, 2002

(65) Prior Publication Data

US 2004/0107967 A1 Jun. 10, 2004

(30) Foreign Application Priority Data

Mar. 14, 2001 (SE) .................................. 0100879

(51) Int. Cl.
*A61M 16/00* (2006.01)
*A62B 19/00* (2006.01)
(52) U.S. Cl. ................... 128/207.16; 128/207.14; 128/205.19; 128/205.12; 128/204.18; 128/200.26
(58) Field of Classification Search ............ 128/204.18, 128/204.21, 204.23, 204.26, 205.12, 205.19, 128/205.24, 206.22, 207.14, 207.15, 207.16, 128/200.26; 604/317, 619
See application file for complete search history.

(56) References Cited

U.S. PATENT DOCUMENTS

| | | | | |
|---|---|---|---|---|
| 2,967,525 A | * | 1/1961 | Stoffregen et al. | 604/147 |
| 2,972,345 A | * | 2/1961 | Spigel | 128/204.23 |
| 3,234,932 A | * | 2/1966 | Bird et al. | 128/204.25 |
| 3,682,166 A | * | 8/1972 | Jacobs | 128/205.19 |
| 3,719,197 A | * | 3/1973 | Pannier et al. | 137/205 |
| 3,991,762 A | * | 11/1976 | Radford | 604/119 |
| 4,233,984 A | * | 11/1980 | Walling | 128/207.14 |
| 4,351,328 A | * | 9/1982 | Bodai | 128/202.16 |

(Continued)

FOREIGN PATENT DOCUMENTS

DE 3907082 2/1990

(Continued)

*Primary Examiner*—Justine R Yu
*Assistant Examiner*—Annette F Dixon
(74) *Attorney, Agent, or Firm*—Venable LLP; Eric J. Franklin

(57) ABSTRACT

A device for a respirator. A tube is operative to be introduced into a trachea of a patient and supply and discharge gas from the patient's lungs. A first conduit connects the tube to the respirator to discharge exhalation gas. A second conduit extends between the tube and a source of sub-pressure. The second conduit is connected to an exhalation tube of the tube. A third conduit connects the tube to the respirator and supplies inhalation gas. In an active position a valve arrangement keeps the second conduit open and connects the exhalation tube to a source of sub-pressure. In an inactive position the valve arrangement keeps the second conduit closed and the first conduit open. A controller moves the valve arrangement from the inactive position to the active position for a period of time to simulate coughing to cause a gas flow to support transport of secretions.

14 Claims, 3 Drawing Sheets

U.S. PATENT DOCUMENTS

| | | | |
|---|---|---|---|
| 4,456,008 A * | 6/1984 | Clawson et al. | 128/205.19 |
| 4,751,924 A * | 6/1988 | Hammerschmidt et al. | 128/207.15 |
| 4,805,611 A | 2/1989 | Hodgkins | |
| 4,867,153 A * | 9/1989 | Lorenzen et al. | 128/205.12 |
| 4,981,466 A * | 1/1991 | Lumbert | 604/19 |
| 5,269,035 A * | 12/1993 | Hartunian | 5/638 |
| 5,315,992 A * | 5/1994 | Dalton | 128/207.15 |
| 5,322,057 A * | 6/1994 | Raabe et al. | 128/203.12 |
| 5,345,928 A * | 9/1994 | Lindkvist | 128/203.12 |
| 5,400,778 A * | 3/1995 | Jonson et al. | 128/205.19 |
| 5,419,314 A * | 5/1995 | Christopher | 128/200.26 |
| 5,582,167 A * | 12/1996 | Joseph | 128/207.15 |
| 5,611,336 A | 3/1997 | Page et al. | |
| 5,676,133 A * | 10/1997 | Hickle et al. | 128/205.12 |
| 6,102,042 A * | 8/2000 | Hete et al. | 128/207.16 |
| 6,298,848 B1 * | 10/2001 | Skog | 128/204.18 |
| 6,550,475 B1 * | 4/2003 | Oldfield | 128/200.26 |
| 6,568,388 B2 * | 5/2003 | Christopher | 128/200.26 |

FOREIGN PATENT DOCUMENTS

| | | |
|---|---|---|
| GB | 2021421 | 12/1979 |
| SE | 182929 | 3/1963 |
| SE | 0000635-3 | 2/2000 |
| SE | 512807 | 5/2000 |
| WO | 93/15782 | 8/1993 |
| WO | 00/13730 | 3/2000 |
| WO | 01/62313 | 8/2001 |

* cited by examiner

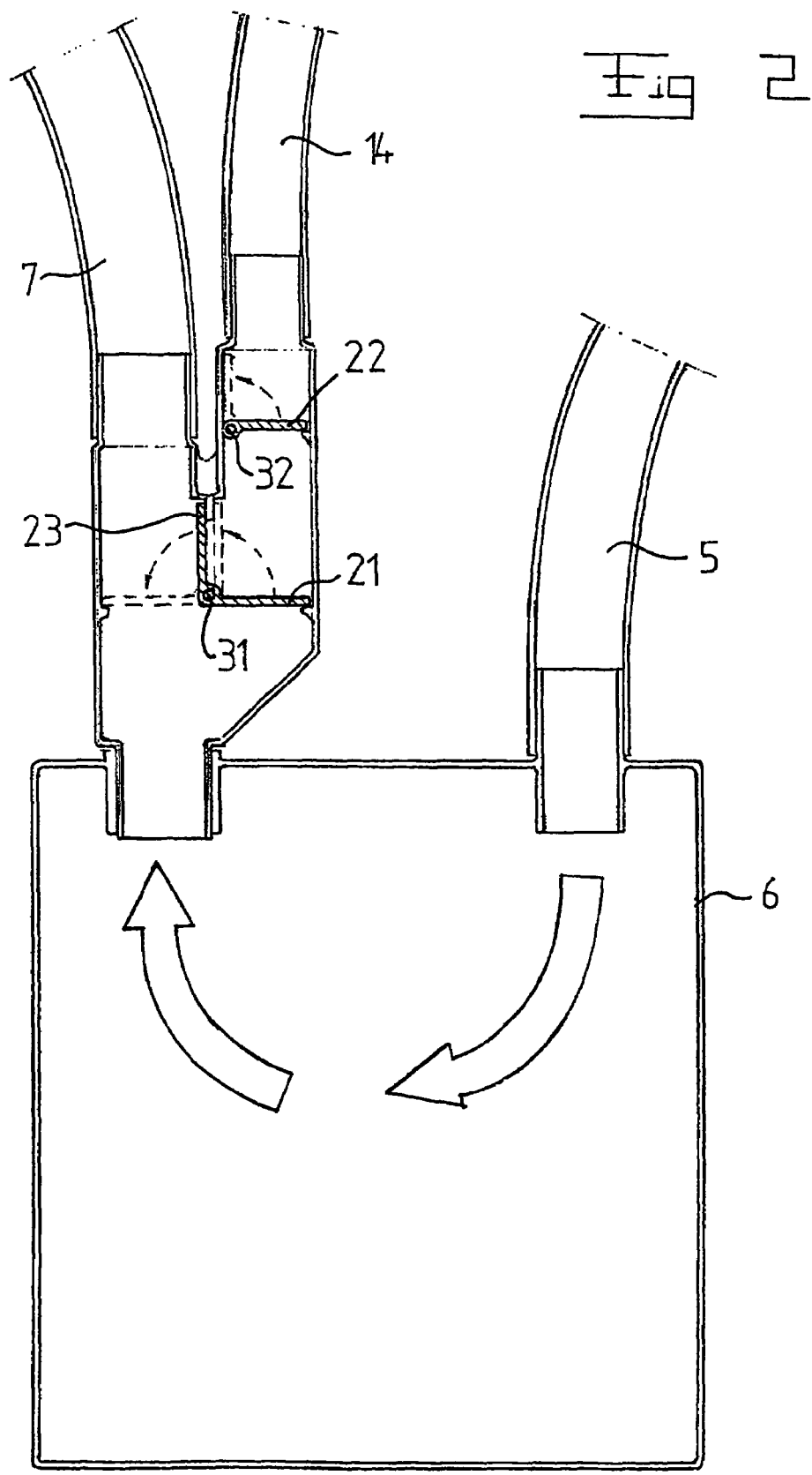

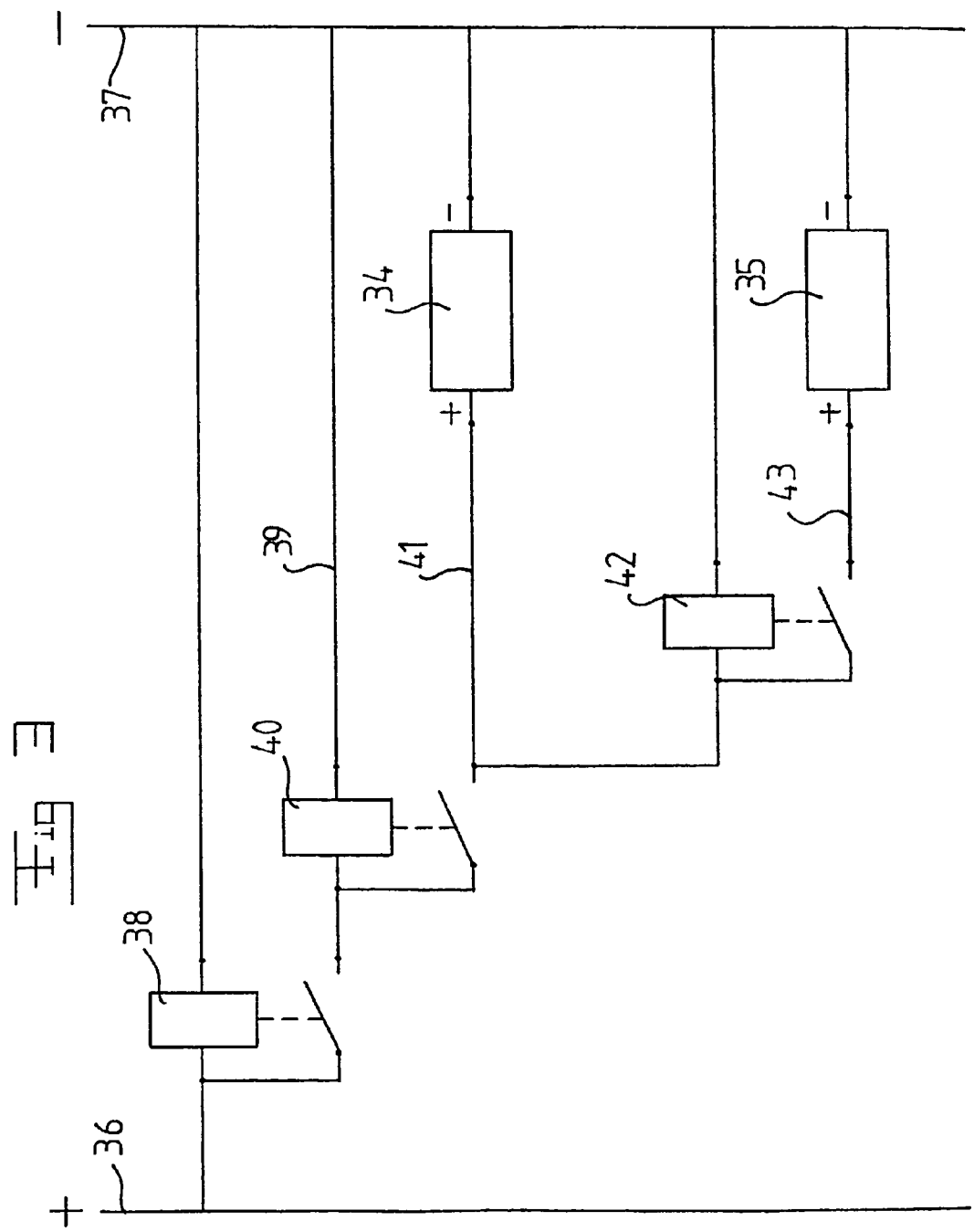

DEVICE FOR A RESPIRATOR

CROSS-REFERENCE TO RELATED APPLICATIONS

This application claims priority to Swedish patent application 0100879-6 filed 14 Mar. 2001 and is the national phase under 35 U.S.C. § 371 of PCT/SE02/00486 filed 14 Mar. 2002.

THE BACKGROUND OF THE INVENTION AND PRIOR ART

The present invention refers to a device for a respirator, which device includes a pipe member arranged to be introduced into the trachea of a patient and which is arranged to supply inhalation gas via the pipe member to the lungs of said patient during a first state and to discharge exhalation gas via the pipe member from the lungs of said patient during a second state.

When a patient is treated by means of a respirator such a pipe member, a so-called endotracheal tube is used, which is a hose that is introduced into the trachea and attached in an airtight manner in the trachea by means of a fixing member, a so-called cuff. Ventilation takes place by supplying air to the lungs during inhalation whereas the exhalation takes place in a passive manner in that the thorax and the diaphragm compress the lungs. The trachea has a natural transport system for transporting secretions upwards. When a conventional endotracheal tube is attached in the trachea, this transport system can not any longer function. The secretions therefore has to be sucked out at regular intervals by means of a catheter which is introduced into the endotracheal tube. Such a catheter suction is combined with a risk of bacterial contamination of the sterile lung region. In connection with the catheter suction or the intermediate accumulation process, movements of accumulations of secretions may generate cough reflexes of the patient. However, resistance from the endotracheal tube does not permit any large or fast air movements, which could contribute to forcing air and thus secretions outwards. During such cough reflexes, the stresses on the fixing member are large. A powerful cough reflex may therefore lead to a spontaneous extubation, i.e. that the endotracheal tube is loosened and makes continued ventilation impossible.

WO-A-00/13730 discloses a device for closed ventilation in which the natural transport system is permitted to function. This known device includes a pipe member, which has a first separate channel for the inhalation gas and a second separate channel for the exhalation gas. In case of a great production of secretions, the second channel could possibly be blocked and thus prevent an efficient gas exchange.

SE-A-0000635-3 discloses a similar device for closed ventilation. This device includes a container for collection of secretions.

GB 2 021 421 discloses a device for a respirator. The device includes a conduit for the supply of inhalation air. The conduit includes a valve arrangement, which permits the exhalation air from a patient to be conveyed out into the environment.

WO93/15782 discloses a device, which is intended to be used during suction of the airways of a patient. During suction a vacuum is applied to the airways. If the pressure in the airways falls below a predetermined value, at which there is a risk of a collapse of the airways, a security valve is open automatically.

U.S. Pat. No. 5,611,336 discloses a device for suction of a patient. The device includes a hose, which is kept in a thin casing and which is intended to be introduced into an endotracheal tube through a protecting member that is applied in front of the mouth of the patient.

SUMMARY OF THE INVENTION

The object of the present invention is to remedy the problems mentioned above and to ensure an efficient transport of secretions from the lungs and the trachea, especially during a respirator treatment.

By means of the second passage, which extends between the pipe member and a source providing a sub-pressure, and the valve arrangement, which in an active position during a short period of time, is arranged to keep the second passage open, it is thus possible to apply instantaneously a temporary short sub-pressure in a passage, which leads the exhalation gas from the lungs. Such a sub-pressure provides a simulated cough reflex of the patient. This simulated cough reflex may contribute to an improved transport of secretions from the lungs and the trachea.

According to an embodiment of the invention, the valve arrangement is, when the second passage is open, arranged to keep the first passage closed. In such a way, it is ensured that the whole sub-pressure is applied to the exhalation gas from the lungs. Advantageously, the valve arrangement is, in an inactive normal position during a main part of the time of use of the device, arranged to keep the second passage closed. At the same time, i.e. when the second passage is closed, the first passage is open for permitting normal transport of the exhalation gas from the lungs.

According to a further embodiment of the invention, the valve arrangement includes a first valve, which is provided between the pipe member and said source and which is arranged to be open in said active position and closed in said inactive normal position. By such a valve, it may thus be ensured that the second passage is closed in the inactive, normal position and shortly open in the active position for sucking secretions and phlegm from the lungs and the trachea.

According a further embodiment of the invention, the valve arrangement includes a second valve, which is provided between the first valve and said source and which is arranged to be open in said active position and closed in said inactive normal position. By means of two such valves of the second passage, the security of the device may be improved. In order to be able to apply a sub-pressure it is required that both the first valve and the second valve are open, i.e. displaced from their closed normal positions.

According to a further embodiment of the invention, the valve arrangement includes a third valve, which is provided between the pipe member and the respirator and which is arranged to be closed in said active position and open in said inactive normal position.

According to a further embodiment of the invention, the device includes a control device for controlling the valve arrangement. The first valve, the second valve and the third valve may then be connected to the control device, which is arranged to control these valves. Advantageously, the control device includes a first unit for controlling the first valve and a second unit for controlling the second valve, wherein these units are substantially independent of each other. Since these units are independent of each other, a high functional security may be obtained because the probability is high that at least one of these units are functioning. By such an embodiment, it is thus ensured that the second passage is not open in an uncontrolled manner and that it does not remain open longer than the predetermined short period of time. Furthermore, the control device may be connected to the respirator for initiating the active position with respect to said state, preferably substantially immediately after one of said first states.

According to further embodiment of the invention, the device includes a container through which at least one of the first passage and the second passage extend for collecting liquid from the exhalation gas. By such a container, secretions and phlegm from the lungs and the trachea may be caught and separated from the exhalation gas.

According to a further embodiment of the invention, the pipe member includes a feeding pipe, which is connected to the third passage and which has an outlet opening arranged to be positioned in trachea during use of the device, and a discharge pipe, which is connected to the first passage and the second passage and which has an inlet opening arranged to be positioned in trachea during use of the device. In such a way it is possible to separate completely the third passage from the first and second passages, i.e. to obtain separate channels for the inhalation gas and the exhalation gas. The secretions that are secreted may thus in an efficient manner be transported away with the exhalation gas without being mixed with the inhalation gas. Said outlet opening may be a distal opening arranged to be positioned at the dividing portion of the main bronchi of the patient during use of the device. Said inlet opening may be provided above said outlet opening. Advantageously, the pipe member may include a fixing member, which is arranged to be introduceable into the trachea and permit airtight fixing of the pipe member in the trachea, wherein the fixing member is arranged to be attached substantially immediately beneath the larynx of the patient and wherein the inlet opening of the discharge pipe is provided substantially immediately beneath the fixing member and at a substantial distance from the outlet opening of the feeding pipe. Furthermore, the pipe member may include a distance member, which is provided around the feeding pipe between said inlet opening and said outlet opening and arranged to ensure that the feeding pipe is located at a distance from at least some part of an inner wall of the trachea.

The device may co-operate with any suitable source for providing an inlet gas and with any suitable vacuum source.

BRIEF DESCRIPTION OF THE DRAWINGS

The present invention is now to be explained more closely by a description of various embodiments disclosed as examples and with reference to the drawings attached.

FIG. 2 discloses a schematic view of a valve arrangement of the device according to the invention.

FIG. 3 discloses a schematic view of a control circuit for controlling the valve arrangement.

DETAILED DESCRIPTION OF VARIOUS EMBODIMENTS OF THE INVENTION

Figure 1:
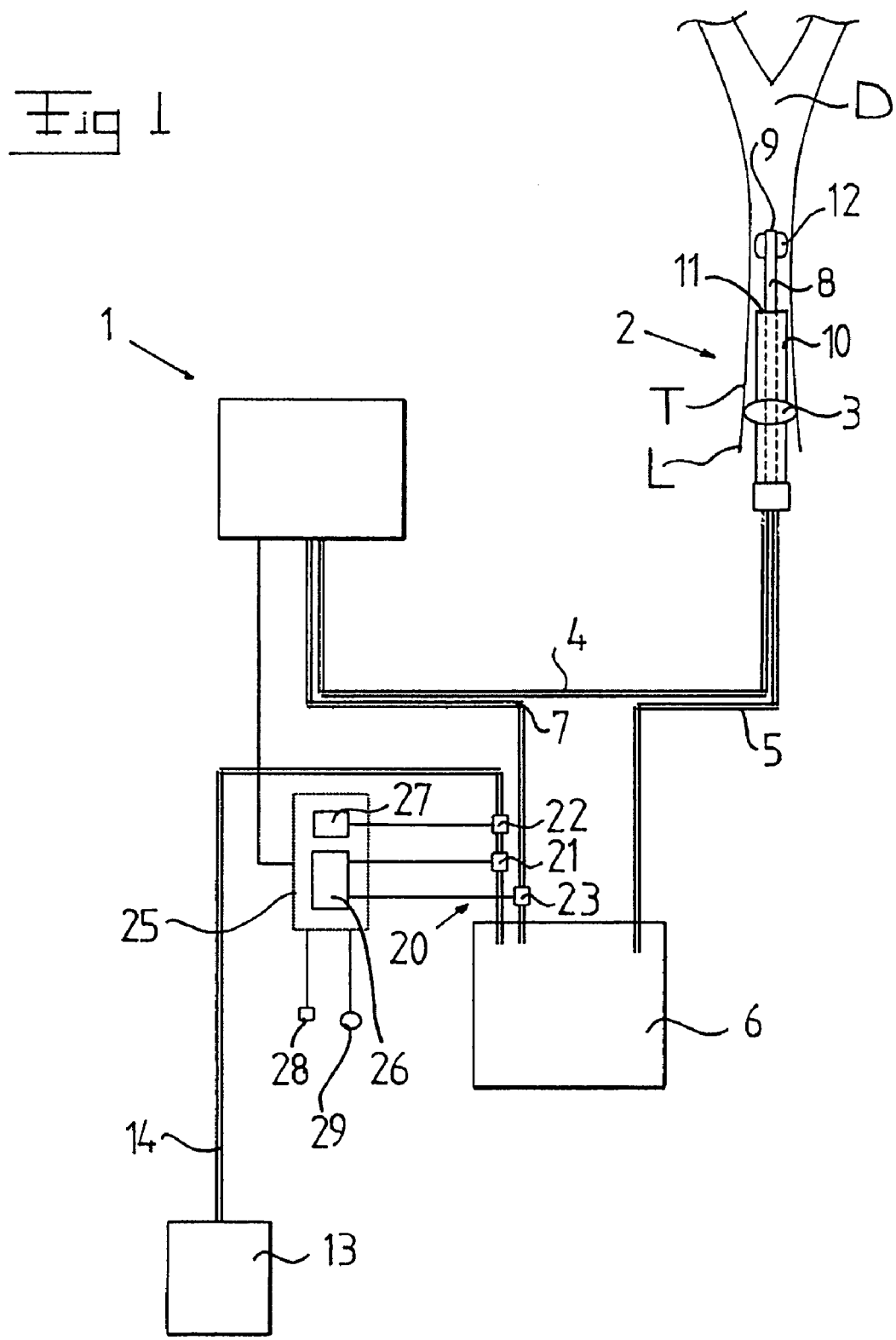
FIG. 1 discloses a schematic view of a device according to the invention.

FIG. 1 discloses a respirator 1, which includes a pipe member 2, which is intended to be introduced into the trachea T of a patient and which may be a so-called endotracheal tube. The pipe member 2 is arranged to be fixed in the trachea by means of a fixing member 3. The fixing member 3, which may be a so-called cuff, includes a swelling body, which is arranged to be expandable to sealing abutment against the inner wall of the trachea by the supply of a medium via a conduit (not disclosed).

The pipe member 2 is connected to the respirator 1 via a (third) passage in the form of a first transport conduit 4 for the supply of inlet gas or breathing gas to the lungs of the patient during a first state for the respirator 1. Furthermore, the pipe member 2 is connected to the respirator 1 via a (first) passage for the discharge of outlet gas or exhalation gas from the patient during a second state for the respirator 1. In the embodiment disclosed, this passage is formed by a second transport conduit 5, a container 6 and a third transport conduit 7. The exhalation gas is thus conveyed from the pipe member 2 through the second transport conduit 5 to the container 6 and from the container 6 through the third transport conduit 7 to the respirator 1. This transport of exhalation gas may be obtained by means of the exhalation of the patient proper, i.e. without any sub-pressure being generated by the respirator 1. The container 6 is in this connection arranged to separate moisture, including condensate, secretions and phlegm, from the exhalation gas and to collect this liquid. The container 6 then includes a collecting part, which in an easy manner may be released and replaced or emptied when it is full.

The pipe member 2 includes a feeding pipe 8, which is connected to the first transport conduit 4 and arranged to feed inlet gas or inhalation gas to the lungs of the patient. The feeding pipe 8 has an outlet opening 9 which in the embodiment disclosed is a distal outlet opening 9 arranged to be positioned in the trachea T and more precisely at the dividing region D of the main bronchi of the patient. Furthermore, the pipe member 2 includes a discharge pipe 10, which is connected to the second transport conduit 5 for transporting exhalation gas from the lungs of the patient. The discharge pipe 10 has an outlet opening 11, which in the embodiment disclosed is a proximal inlet opening 11, which is provided above said outlet opening 9, i.e. further away from the dividing region of the main bronchi than the outlet opening 9. The fixing member 3 is arranged to be attached substantially immediately beneath the larynx L of the patient. The inlet opening 11 of the discharge pipe 10 is provided substantially immediately beneath the fixing member 3 and at a substantial distance from the outlet opening 9 of the feeding pipe 8.

Furthermore, the pipe member 2 includes a distance member 12, which is provided around the feeding pipe 8 between the inlet opening 11 and the outlet opening 9. The distance member 12 ensures that the feeding pipe 8 is located at a distance from some part of an inner wall of the trachea of the patient.

The device according to the invention includes a further (second) passage, which connects the pipe member 2 with a source 13 providing a sub-pressure. This sub-pressure is substantially lower than the pressure prevailing in the third transport conduit 7. This further passage extends from the pipe member 2, and more precisely from the inlet opening 11 and the discharge pipe 10, through the second transport conduit 5, the container 6 and a fourth transport conduit 14 to the source 13. The source 13 may, for instance, be formed by a separate vacuum pump or obtained by means of pressurised air, which is available centrally in, for instance, a hospital. In the embodiment disclosed, the passage 5-7 and the passage 5, 6, 14 have a common container 6 for collecting liquid from the exhalation gas. However, it is to be noted that these passages may be provided with a respective separate such container.

By means of a valve arrangement 20, the outlet gas or exhalation gas from the patient can be guided from the second transport conduit 5 and the container 6 to either the third transport conduit 7 or the fourth transport conduit 14. When the valve arrangement 20 is adjusted in such a way that the exhalation gas is conveyed to the respirator 1 via the third transport conduit 7, the device is in an inactive normal position. When the valve arrangement 20 is adjusted in such a way that the exhalation gas is conveyed to the source 13 via the fourth transport conduit 14, the device is in an active position.

The device is mainly in the inactive normal position and is arranged to be in the active position during merely short periods of time of in the order of 0.5-3 seconds, preferably approximately 1 second. The vacuum applied can, but does not need to be applied continuously during these periods of time but may also be applied intermittently, i.e. during a period of time of the active position a pulsating vacuum is applied.

The valve arrangement 20 includes a first valve 21, a second valve 22 and a third valve 23. The first valve 21 is provided between the pipe member 2 and the source 13. The first valve 21 is open in the active position and closed in the inactive normal position. The second valve 22 is provided between the first valve 21 and the source 13. Also the second valve 22 is open in the active position and closed in the inactive normal position. The pulsating vacuum may for instance be obtained by alternately opening and closing the second valve 22 at a high frequency. The third valve 23 is provided between the pipe member 2 and the respirator 1. The third valve 23 is closed in the active position and opened in the inactive normal position.

The device also includes a control device 25 for controlling the valve arrangement 20, and more precisely the first valve 21, the second valve 22 and the third valve 23, which in the embodiment disclosed all are connected to the control device 25. The control device 25 includes a first unit 26 for controlling the first valve 21 and the third valve 23, and a second unit 27 for controlling the second valve 22. The two units 26 and 27 are substantially independent of each other. It is of course also possible to let the control device 25 include three separate control units, one for each valve 21-23.

The control device 25 is connected to the respirator 1 and arranged to receive a signal from the respirator 1. The respirator 1 senses, according to previously known technique, an obstruction in the airways, for instance when two much secretions or phlegm have been collected in the airways. The respirator 1 then delivers, for instance when the breathing resistance exceeds a predetermined level, in an automatic manner said signal to the control device 25, which utilizes the signal for initiating the active position with respect to in which of said first and second states the respirator 1 is. The signal is delivered substantially immediately after one of said first states or substantially immediately before one of said second states. In other words, the active position may be initiated first when the inhalation has been completed and before the exhalation has been started, i.e. when there is a maximum of gas in the lungs. The respirator 1 may also be arranged to sense a coughing or a cough attempt from the patient and as a response thereto deliver said signal.

The device may also include a member 28 for manually initiating the active position, for instance when a nurse estimates that the patient has too much phlegm in the airways. Furthermore, the device may include members 29, which warn the patient immediately before an initiating of the active position is to take place. Such a warning member 29 may for instance be realised by a light emitting diode and/or any light or sound generating member.

The control device 25 is arranged to control the valve arrangement 20 in such a way that the third valve 23 is open at the same time as the first valve 21 and the second valve 22 are closed in the inactive normal position. When the device is to be activated, the third valve 23 is closed at the same time as the first valve 21 and the second valve 22 are open during the short period of time mentioned above. This short period of a sub-pressure will simulate a coughing, i.e. cause a quick and powerful flow of gas from the lungs and the trachea, which flow brings secretions and phlegm from the lungs.

The valves 21-23 and the control device 25 with the different units 26, 27 may be realized in many different manners. FIG. 2 discloses schematically an example of design of the valves 21-23. The first valve 21 and the third valve 23 are here connected to each other and rotatable about a common rotary axis 31. In a first rotary position corresponding to the inactive normal position, the valves 21 and 23 are positioned in such a way that the first valve 21 closes the fourth transport conduit 14 and the third valve 23 keeps the third transport conduit 7 open. By rotating one of the valves 21 and 23 approximately 90° about the rotary axis 31 to a second rotary position, corresponding to the active position, the first valve 21 will open the fourth transport conduit 14 and close the third transport conduit 7. The second valve 22 is rotatable about a separate rotary axis 32 and may thus be controlled independently of the valves 21 and 23. In a first rotary position, corresponding to the inactive normal position, the second valve 23 closes the fourth transport conduit 14. In a second rotary position, corresponding to the active position, the second valve 22 keeps the fourth transport conduit 14 open.

FIG. 3 discloses an example of a control circuit for controlling the valves 21-23, which for instance may be realised by means of so-called magnet valves. A first three-way magnet valve 34 forms the first valve 21 and the third valve 23. A second two-way magnet valve 35 forms the second valve 22. The control circuit is connected to the respirator 1 via the electric conduit 36 and 37. When the respirator 1 delivers said signal via the conduits 36, 37, a first relay 38 is activated, which relay closes a first subcircuit 39 during an adjustable first time interval, for instance 2 s. The first subcircuit 39 includes a second relay 40. The second relay 40 will then be activated and close a second subcircuit 41 during an adjustable second time interval, for instance 1.5 s. The second subcircuit 41 includes the first magnet valve 34 and a third relay 42. The magnet valve 34 will then close the third valve 23 and open the first valve 21. In addition, the third relay 42 will close a third subcircuit 43 during a third time interval, for instance 1 s. The third subcircuit 43 includes the second magnet valve 35. The second magnet valve 35 will then open also the second valve 22 and exhalation gas may at a high velocity flow from the lungs of the patient towards said source 13, wherein secretions and phlegm is caught by the container 6.

The present invention is not limited to the embodiment disclosed but may be varied and modified within the scope of the following claims. For instance, it is to be noted that the invention also is applicable to a more conventional endotracheal tube with a pipe member including one single common channel for the inlet gas or inhalation gas and the outlet gas or exhalation gas.

The device according to the invention may also function together with any suitable source 1 for providing an inlet gas but not necessarily a respirator. Such a source 1 may permit feeding of an inlet gas only for the purpose of filling the lungs with gas for permitting the subsequent vacuum suction described above.

The outlet opening 9 of the feeding pipe 8 and the inlet opening 11 of the discharge pipe 10 may also be positioned at another level than the ones disclosed. For instance, these openings can be positioned at the same level in trachea.

The invention claimed is:

1. A cough-simulating device operative to be used together with a respirator during respirator treatments, the cough-simulating device comprising:
 a tube member operative to be introduced into a trachea of a patient and to supply inhalation gas to and discharge exhalation gas from lungs of the patient, the tube member comprises an inhalation tube to supply the inhalation gas and an exhalation tube separate from the inhalation tube to discharge the exhalation gas separately from the inhalation gas, the inhalation tube comprising an outlet opening operative to be positioned in the trachea of the patient, and the exhalation tube comprising an inlet opening operative to be positioned in the trachea of the patient;

a first conduit operative to connect the exhalation tube to the respirator and to permit said discharge of exhalation gas;

a second conduit operative to connect the exhalation tube to a source providing a sub-pressure;

a third conduit operative to connect the tube member to the inhalation tube and to supply the inhalation gas;

a valve arrangement moveable between an active position and an inactive normal position, wherein in the active position the valve arrangement is operative to keep the second conduit open and to connect the exhalation tube to the source, and in the inactive normal position the valve arrangement is operative to keep the second conduit closed and to keep the first conduit open; and a controller operatively connected to the respirator to initiate the active position substantially immediately after an inhalation for a short period of time to simulate a coughing of the patient when breathing resistance exceeds a predetermined level, thereby causing a gas flow supporting a transport of secretions through airways of the patient and through the exhalation tube during the respirator treatment.

2. The device according to claim 1, wherein the valve arrangement is operative to keep the first conduit closed when the second conduit is open.

3. The device according to claim 1, wherein the valve arrangement comprises a first valve that is arranged between the tube member and the source of sub-pressure and that is open in the active position.

4. The device according to claim 3, wherein the valve arrangement comprises a second valve that is arranged between the first valve and the source of sub-pressure and that is open in the active position.

5. The device according to claim 4, wherein the second valve is closed in the inactive position.

6. The device according claim 4, wherein the valve arrangement comprises a third valve that is arranged between the tube member and the respirator and that is closed in the active position.

7. The device according to claim 6, wherein the third valve is open in the inactive position.

8. The device according to claim 6, wherein the controller is operatively connected to the first valve, the second valve and the third valve.

9. The device according claim 4, wherein the controller comprises a first unit operative to control the first valve and a second unit operative to control the second valve, wherein the first unit and the second unit are substantially independent of each other.

10. The device according to claim 1, wherein the first valve is closed in said inactive position.

11. The device according claim 1, further comprising:
a container through which at least one of the first conduit and the second conduit extends for collecting liquid from the exhalation gas.

12. The device according to claim 1, wherein the outlet opening of the inhalation tube is a distal outlet opening operative to be positioned at a dividing region of a main bronchi of the patient during use of the device, and wherein the inlet opening of the exhalation tube is arranged above the outlet opening of the inhalation tube.

13. The device according to claim 12, wherein the tube member further comprises a fixing member that is operative to introduced into the trachea and permit airtight fixing of the tube member in the trachea, wherein the fixing member is operative to be arranged substantially immediately below a larynx of the patient and wherein the inlet opening of the exhalation tube is arranged substantially immediately beneath the fixing member and at a substantial distance from the outlet opening of the feeding pipe.

14. The device according to claim 13, wherein the tube member further comprises a distance member arranged around the inhalation tube between the inlet opening and the outlet opening and arranged to ensure that the inhalation tube is located at a distance from at least one part of an inner wall of the trachea.

* * * * *